(12) United States Patent
Biegun et al.

(10) Patent No.: US 6,802,865 B2
(45) Date of Patent: Oct. 12, 2004

(54) TILTED FEMORAL COMPONENT

(75) Inventors: Jean-François Biegun, Chaumont (FR); Pascal Marceaux, Chaumont (FR)

(73) Assignee: Aesculap (FR)

( * ) Notice: Subject to any disclaimer, the term of this patent is extended or adjusted under 35 U.S.C. 154(b) by 63 days.

(21) Appl. No.: 09/981,594

(22) Filed: Oct. 17, 2001

(65) Prior Publication Data

US 2002/0045947 A1 Apr. 18, 2002

(30) Foreign Application Priority Data

Oct. 18, 2000 (FR) .............................................. 00 13313

(51) Int. Cl.$^7$ ................................................. A61F 2/38
(52) U.S. Cl. .................................. 623/20.35; 623/20.21
(58) Field of Search ........................... 623/20.14, 20.21, 623/20.31, 20.35, 20.36, 20.28

(56) References Cited

U.S. PATENT DOCUMENTS

| | | | | |
|---|---|---|---|---|
| 5,133,758 A | * | 7/1992 | Hollister | ................... 623/20.31 |
| 5,326,361 A | * | 7/1994 | Hollister | ................... 623/20.21 |
| 5,681,354 A | | 10/1997 | Eckhoff | ........................ 623/20 |
| 5,824,105 A | | 10/1998 | Ries et al. | ...................... 623/20 |
| 6,013,103 A | | 1/2000 | Kaufman et al. | .............. 623/20 |
| 6,210,443 B1 | * | 4/2001 | Marceaux et al. | ........ 623/20.33 |
| 6,458,160 B2 | * | 10/2002 | Biegun et al. | ............ 623/20.27 |
| 6,540,787 B2 | * | 4/2003 | Biegun et al. | ............ 623/20.31 |

FOREIGN PATENT DOCUMENTS

DE 89 11 095.1 9/1990 .............. A61F/2/38

* cited by examiner

*Primary Examiner*—Corrine McDermott
*Assistant Examiner*—Kamrin R. Landrem
(74) *Attorney, Agent, or Firm*—Renner, Kenner, Greive, Bobak, Taylor & Weber

(57) ABSTRACT

The femoral component of a knee prosthetic includes a trochlean part (3) and at least one, but preferably two condyles (2) wherein a trochlean trajectory is defined within the external surface of the component by the trochlea. A set of internal flat sides (5, 6, 7, 8 and 9) are implemented to make contact with corresponding re-cut sides of the extremity of the femur and define an internal open cage within the internal surface of said component and further define edges (15, 16, 17 and 18) between themselves. The perpendicular projection (4) of said trochlean trajectory in the medial lateral perspective of said femoral component has a tilt angle (alpha) with a value different from zero relative to the line (23) perpendicular to the perpendicular projection of said edges in said medial lateral perspective.

13 Claims, 2 Drawing Sheets

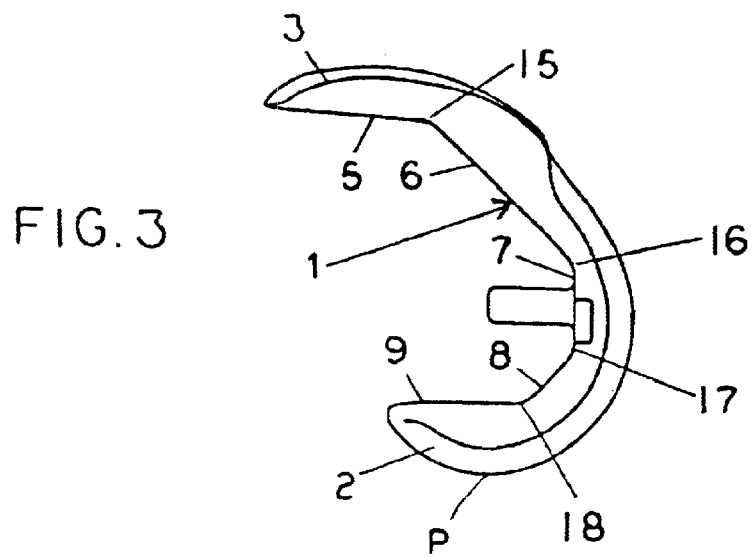
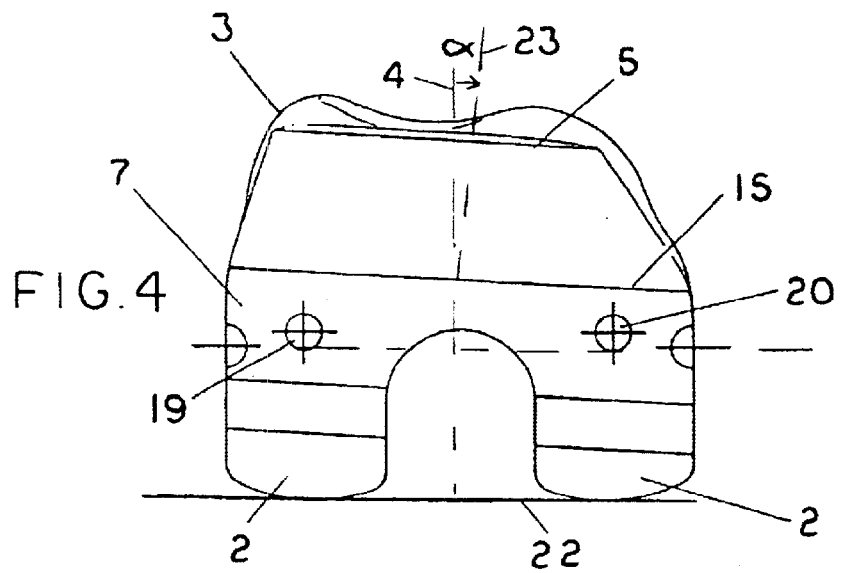
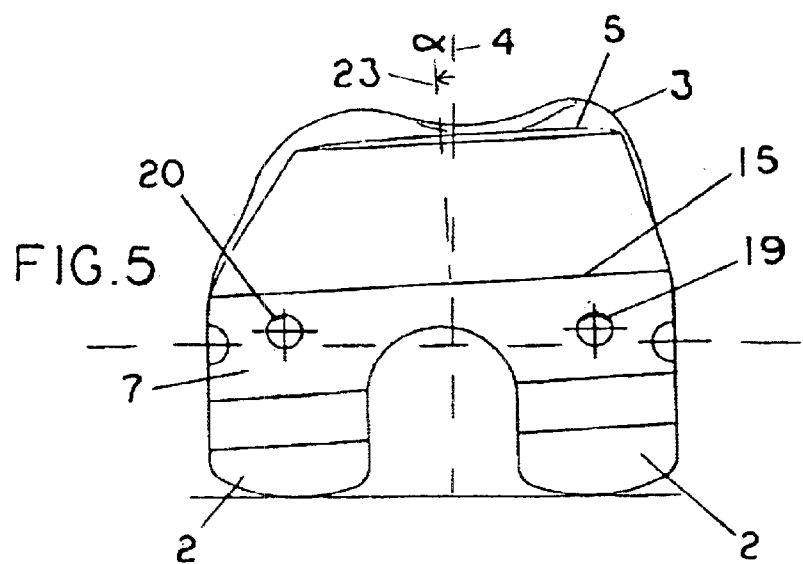

TILTED FEMORAL COMPONENT

BACKGROUND OF THE INVENTION

1. Field of the Invention

The present invention relates to a femoral component which co-operates with a tibia plate, eventually including the interposition of an insert or tibia meniscus applied to said tibia plate, as well as a knee prosthetic including a femoral component of this type.

2. Description of the Related Art

According to the prior art, femoral components include a trochlea and at least one, but preferably two, condyles and a trochlean trajectory is defined by said trochlea within the external surface of said component. Said femoral component also includes a set of internal flat sides, the purpose of which is to make contact with the corresponding re-cut sides of the distal extremity of a femur, said internal flat sides being implemented within the internal surface of said component and the combination of which defines internal edges.

In order to apply tibia prosthetics of the type described above, notably when it is preferable to anchor a femoral component of the type described thereabove to the proximal extremity of a femur, the extremity of said femur is initially cut or re-cut. Generally, said re-section is carried out such that the extremity of the femur includes a plurality of sides separated between themselves by edges. One of said sides is preferably perpendicular to the axis defined by the femur, whereas the other sides are tilted relative to said one of said sides.

Similarly, when implementing said prosthetic, the tibia must also be re-cut an one side located at the distal extremity of said tibia, which is preferably perpendicular to the longitudinal axis of the tibia.

For a given knee prosthetic, the medial side and the lateral side of said prosthetic is defined. The lateral medial side is the side parallel to the tibia axis and also includes the axis of the other tibia. The medial side is therefore the side of the prosthetic located on the side of the other prosthetic or the other healthy knee of the patient and the lateral side is therefore the side located on the outside of said patient, relative to said given prosthetic.

When a tibia is cut following what is known in the art as a neutral cut as previously defined, i.e. a cut which forms a flat side perpendicular to the axis of the tibia, more bone is taken off the upper lateral side of the tibia than the upper medial side of said tibia. However, the neutral out of the femur results in the same quantity of bone taken off both the medial and lateral condyles. Consequently, there exists a trapezoidal volume between the re-cut tibia and the femur as opposed to a parallelogram before the prosthetic is manufactured and applied. Indeed, the distance between the tibia and the femur perpendicularly to the lateral side of the re-cut tibia side is greater than the same distance on the medial side.

This trapezoidal volume is a disadvantage. Indeed, its existence may result in a medial collateral ligament too tightly wound or a lateral collateral ligament to loosely wound. Consequently, in order to avoid the formation of said trapezoidal volume, an external rotation of the femur is implemented when attaching said femur. As the femur is turned, more bone is taken off at the medial level than at the lateral level such that a rectangular volume is created. However, a plurality of disadvantages result from the above external rotation of the femur, notably when a cutting operation results in more medial bone being taken off than lateral bone;

1) Firstly, the proximal trochlean trajectory is laterally skewed whereas the dovetail is distally brought back towards the medial side when the femur is turned externally. Thus, once the prosthetic is applied, the truchlea moves in the medial direction across a middle line when the knee is bent. The fact of "medialising" the trochlean trajectory may contribute to an incorrect positioning of the trochlea whilst it moves, which may therefore engender pain, a fracture, a loosening or premature wearing.

2) Moreover, it would also be reasonable to turn the tibia externally in order to align the femur and the tibia in a stretched position of the knee when the femur is turned externally. The base plate of the tibia prosthetic may therefore extend beyond the bone, such that a surgeon must implement a smaller tibia component in order b avoid this situation. If a small tibia prosthetic is implemented, the general cover of the bone will be reduced, which should also be avoided.

3) Moreover, the femoral components of the tibia must be aligned relative to a rotation over a comprehensive domain of movements in order to reduce the wearing of the polythene material of the insert located in-between. Indeed, when both the femoral and tibia components are externally turned, the contact area between the femur and the tibia is maximised when the knee is extended but decreases as said knee is flexed, i.e. the congruence becomes less adequate.

If the tibia component is located according to a neutral location with a femoral component turned eternally, the congruence is reduced when the knee is flexed but increases as the knee extends. Therefore, the contact area is maximised when the knee is flexed but reduced when said knee extends. Thus, independently of the orientation of a tibia component, the congruence cannot be maintained within the entire flexing domain when the femur is externally turned. The above eventually becomes a very important factor or parameter with knee implementations requiring high confirmation.

Implementing an external rotation of the femur removes more bone on the anterior lateral side and thus increases the probability of a notch forming up. This may weaken the femur to breaking point, which should be avoided.

5) Finally, an inappropriate removal of bone from the anterior medial femur may create a space between the prosthetic and the bone and thus compromise the correct positioning of the prosthetic.

A particular prosthetic is known which is described in the German utility model number G 89 11 095.1 in the name of Miehlke, amongst prosthetics according to the prior art. In this prosthetic, the edges of the cages are tangentially parallel to the condyles in their most distal part, and the trochlean trajectory is tilted relative to a perpendicular line extending from said tangential plane (or reference line defined by the condyles when they are resting horizontally).

A particular prosthetic known according to the prior art is also described in U.S. Pat. No. 5,824,105 in the name of Ries. The edges are also tangentially parallel to the condyles in their most distal part and the trochlean trajectory is perpendicular to this plane, with a bevelled insert located between the tibia plate and the condyles in order to best fill the trapezoidal space shown in FIG. 1.

Another femoral prosthetic of the known prior art is described in U.S. Pat. No. 5,326,361 in the name of Hollister. In the specification, the cage (the edges) is tilted relative to the tangential plane defined by the condyles (or reference line) and the trochlean trajectory is also tilted relative to a perpendicular line extending from said tangential plane. Finally, the prosthetic described in U.S. Pat. No. 6,013,103 in the name of Kaufman teaches a cage which is tangentially parallel to the condyles and a trochlean trajectory tilted relative to a perpendicular line extending from said tangential plane.

The present invention proposes to solve the above described disadvantages and notably proposes a new femoral component which solves the problem that arises from the neutral re-section of the tibia, i.e. the presence of a trapezoidal space between the re-out tibia and the re-out femur without implementing an external rotation of the femur when it s re-out.

BRIEF SUMMARY OF THE INVENTION

According to the present invention, the disadvantages that arise from the external rotation of the femur are remedied as said external rotation is not required anymore and, at the same time, the ligament collateral to the prosthetic is not subjected to a variable stress between the medial side and the lateral side of the prosthetic.

According to the invention, a femoral component of a knee prosthetic includes a trochlean part and at least one, but preferably two condyles, said trochlean trajectory being defined within the trochlean part within the external surface of the component and a set of internal flat sides which will make contact with the corresponding re-cut sides of the distal extremity of a femur. Said internal flat sides define an internal open cage within the internal surface of the component, said internal flat sides further define internal edges between themselves, said condyles define a reference line when horizontally positioned, which corresponds to the contact line with said horizontal plane. Said femoral component of a knee prosthetic is characterised in that the perpendicular projection of the trochlean trajectory relative to the medial lateral plane is perpendicular to said reference line and said edges are tilted by a tilt angle with a value different from zero relative to said reference line when orthogonally projected over the medial lateral plane.

As the internal sides of the femoral component are tilted relative to the tibia plane onto which the condyles are positioned, i.e. as the cages are tilted, said trapezoidal space is perfectly filled and therefore there results an equal stress on either side of the prosthetic applied to the ligaments collateral to said prosthetic, without however requiring an external rotation of the femur component, wherein said external rotation would result in important disadvantages.

According to a preferred embodiment of the present invention, the internal open cage includes five flat sides.

According to a preferred embodiment of the present invention, the external shape of said condyles is spherical.

According to a preferred embodiment of the present invention, the inclination angle corresponds to the angle according to which the femur must be rotated in the case of the said method of external rotation of the femur, such that said method is no longer required.

The present invention also relates to a couple of femoral components as previously described, i.e. a left femoral component and a right femoral component, wherein the inclination angle is calculated clockwise in the case of the left prosthetic and anti-clockwise in the case of the right prosthetic.

The present invention also relates to a complete knee prosthetic including a component as previously described, co-operating With a tibia plate, wherein a meniscus or tibia inset, preferably in polythene material, is eventually positioned in-between said tibia plate and said component.

BRIEF DESCRIPTION OF THE SEVERAL VIEWS OF THE DRAWINGS

FIG. 3 shows a side view of a femoral component according to the invention, as viewed from the right of the prosthetic of FIG. 4.

FIG. 4 is a representation in the medial lateral perspective of the component shown in FIG. 3, in the case of a left prosthetic and FIG. 5 is representation in the medial lateral perspective of the prosthetic shown in FIG. 3 in the case of a right prosthetic.

BEST MODE FOR CARRYING OUT THE INVENTION

Figure 1:
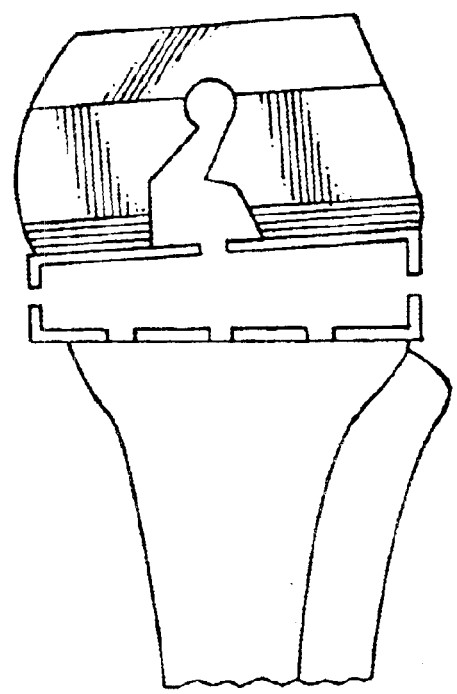
FIG. 1 shows a flexed knee, the femur and tibia of which were re-cut, without an external rotation of the femur.

The invention will now be described by way of example only with reference to the previously identified drawings.

The femoral component 1 shown in FIG. 3 includes two condyles 2 and a trochlear 3. Said trochlear 3 defines a trochlean trajectory, the projection 4 of which is shown in FIG. 4 as the medial lateral perspective. The external surface of each condole 2 has a circular shape, as shown in the perspective of FIG. 3, which is also the antero-posterior plane. The same applies for trochlear 3, the trochlean trajectory also having a circular shape. Five flat sides 5, 6, 7, 8 and 9 are defined within the inside of the femoral component 1, first defining an open cavity. Said five flat sides 5, 6, 7, 8 and 9 are separated from one another by edges 15, 16,17 and 18. Two pins 19 and 20 are implemented on the internal side 7, onto which the re-cut femur will anchor. The internal sides, 5, 6, 7, 8 and 9 correspond to the sides re-cut within the femur shown in FIG. 1, both in dimension and inclination. The edges and notably edge 15 are inclined by an angle alpha of 3 degrees in the medial lateral perspective, relative to a plane 22 which is perpendicular to the perpendicular projection 4 of the trochlean trajectory in the perspective shown in FIG. 4 (medial lateral perspective). Said tilt angle alpha varies according to the femur of each individual, the value of which generally lays between one and ten degrees, preferably between two and five degrees. From an external point of view, the femoral component according to the invention retains the same aspect as prosthetics according to the prior art. However, the internal cage has been shaped as turned relative to the cages of the known prior art. Cages according to the prior art were shaped to be parallel to the prosthetic whereas the internal cage of the invention is shaped to be slightly tilted relative to the prosthetic.

FIG. 4 shows a left prosthetic in a perspective parallel to the tibia. The angle between the projection of the trochlean trajectory in a medial lateral perspective and the line 23 perpendicular to the projection of the edge 15 in the same perspective equals minus three degrees, and the rotation takes place according to the negative trigonometric direction.

Said angle is shown with a positive value of three degrees in FIG. 5, as the rotation takes place anti-clockwise, i.e. according to the positive trigonometric direction. It is therefore a prosthetic for a right leg.

Figure 2:
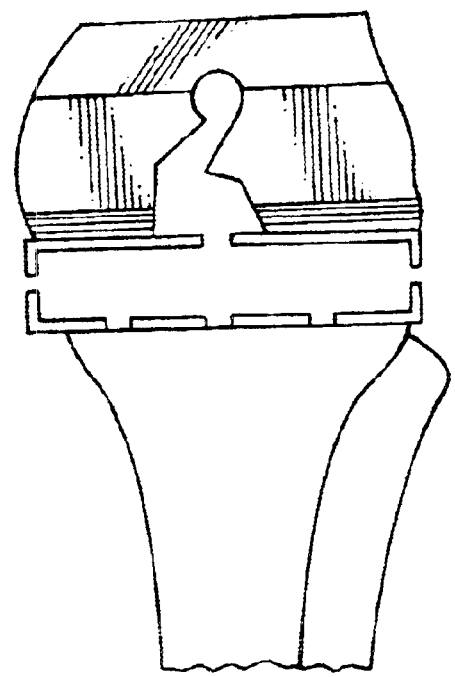
FIG. 2 shows a knee similar to FIG. 1, wherein the femur has however been externally rotated.

FIG. 1 shows the femur bone and tibia bone re-out before a prosthetic is applied, without however applying an external rotation to said femur. FIG. 2 shows the same re-cut bones in the scope of the present invention, wherein the femur is externally rotated. The respective tilt angles of the two components have the same absolute value.

The compact line of the condyles with a horizontal surface onto which they are applied is the reference line. The line 22 perpendicular to the perpendicular projection 4 of the trochlean trajectory in the perspective of FIG. 4 is also the reference line 22.

What is claimed is:

1. The femoral component of a knee prosthetic including a trochlean part and at least one condyle, wherein
   a trochlean trajectory is defined within the trochlean portion in the external surface of the component;
   a set of internal flat sides are implemented to make contact with corresponding re-cut sides of the extremity of the femur and define an internal open cage within the internal surface of said component and further define edges between themselves;
   wherein said condyle, when contacting a horizontal plane, defines a reference line;
   the perpendicular projection of said trochlean trajectory is perpendicular to said reference line in a medial lateral perspective and the edges have a tilt angle with a value different from zero relative to said reference line when orthogonally projected within a medial lateral perspective.

2. The component according to claim 1 wherein said internal open cage includes five flat sides.

3. The component according to claim 1 wherein the external shape of said condyle is spherical.

4. The component according to claim 1, wherein said tilt angle has an absolute value between one and ten degrees.

5. A couple of femoral components according to claim 1, wherein the respective tilt angles of both components have opposite trigonometric sides.

6. A couple of femoral components according to claim 6, wherein said respective tilt angles of both components have the same absolute value.

7. A Knee prosthetic including a tibia plate and femoral component according to claim 1.

8. A Knee prosthetic including a tibia plate and femoral component according to claim 2.

9. A Knee prosthetic including a tibia plate and femoral component according to claim 3.

10. A Knee prosthetic including a tibia plate and femoral component according to claim 1.

11. A Knee prosthetic including a tibia plate and femoral component according to claim 4.

12. The component according to claim 4, wherein said tilt angle is between about 2 and 5 degrees.

13. The component according to claim 12, wherein said tilt angle is 3 degrees.

* * * * *